(12) United States Patent
Pacetti et al.

(10) Patent No.: US 8,367,090 B2
(45) Date of Patent: *Feb. 5, 2013

(54) COATING ON A BALLOON COMPRISING A POLYMER AND A DRUG

(75) Inventors: Stephen D. Pacetti, San Jose, CA (US); John Stankus, Campbell, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 976 days.

This patent is subject to a terminal disclaimer.

(21) Appl. No.: 12/205,577

(22) Filed: Sep. 5, 2008

(65) Prior Publication Data

US 2010/0063570 A1 Mar. 11, 2010

(51) Int. Cl.
*A61F 2/86* (2006.01)
*A61K 31/047* (2006.01)
*A61K 31/075* (2006.01)
*A61K 31/12* (2006.01)
*A61K 31/215* (2006.01)
*A61K 31/41* (2006.01)
*A61K 31/435* (2006.01)
*C08F 118/02* (2006.01)
*C08F 16/12* (2006.01)

(52) U.S. Cl. ........ 424/422; 424/423; 514/731; 514/511; 514/277; 514/290; 514/691; 514/293; 514/1.1; 526/319; 526/333

(58) Field of Classification Search .......... None
See application file for complete search history.

(56) References Cited

U.S. PATENT DOCUMENTS

| | | | |
|---|---|---|---|
| 7,910,678 B2* | 3/2011 | Pacetti | 526/329.6 |
| 2006/0020243 A1* | 1/2006 | Speck et al. | 604/103.02 |
| 2006/0051390 A1* | 3/2006 | Schwarz | 424/422 |
| 2006/0088571 A1* | 4/2006 | Chen et al. | 424/426 |
| 2007/0282419 A1* | 12/2007 | Hilaire et al. | 623/1.11 |
| 2008/0118544 A1* | 5/2008 | Wang | 424/423 |
| 2008/0147178 A1 | 6/2008 | Pacetti et al. | |
| 2010/0145266 A1* | 6/2010 | Orlowski | 604/96.01 |

FOREIGN PATENT DOCUMENTS

WO WO 2008/089730 7/2008

OTHER PUBLICATIONS

WorldNet definition of prevention, Accessed Mar. 2011.*
Restenosis Merck Manual, Accessed Mar. 2011.*
Jorgensen et al. Journal of the American College of Cardiology, vol. 35, No. 3, 592-599, published 2000.*
Sortomer Application Bulletin, Published Dec. 2004, Accessed Mar. 2011.*
Rivera et al. (Molecular Cancer Therapeutics, vol. 10, Issue 6, Published Jun. 2011, pp. 1059-1071).*
Aslamazova et al, "Structure and Properties of Polybutyl Methaclylate Obtained by Polymerization in the Presence of Aerosil", Polymer Science vol. 25, No. 6, pp. 1484-1490 (1983).
Harper, "Drug Latentiation", Prog. Drug. Res., 4: pp. 221-294 (1962).
Kocakulak et al., "Investigation of Blood Compatibility of PMEA Coated Extracorporeal Circuits", J. of Bioactive and Compatible Polymers 17; 33, pp. 343-356 (2002).
Martin et al, "Enhancing the biological activity of immobilized osteopontin using a type-1 collagen affinity coating", Wiley Periodicals, Inc. pp. 10-19 (2004).
Rotterdam et al., "A Randomized Comparison of the Value of Additional Stenting After Optimal Balloon Angioplasty for Long Coronary Lesions", J. of Am. College of Cardiology vol. 39, No. 3, pp. 393-399 (2002).
Sinkula et al., "Rationale for Design of Biologically Reversible Drug Derivatives: Prodrugs", J. of Pharmaceutical Sciences vol. 64, No. 2, pp. 181-210 (1975).
Spagnuolo et al., "Gas1 is induced by VE-cadherin and vascular endothelial growth factor and inhibits endothelial cell apoptosis", Blood, vol. 103, No. 8, pp. 3005-3012 (2004).
Stella et al., "Prodrugs Do They Have Advantages in Clinical Practice?", Drugs 29: pp. 455-473 (1985).
Tanaka et al., "Blood compatible aspects of poly(2-methoxyethylacrylate) (PMEA)-relationship between proteing adsorption and platelet adhesion on PMEA surface", Biomaterials 21, pp. 1471-1481 (2000).
Völkel et al., "Targeting of immunoliposomes to endothelial cells using a single-chain Fv fragment directed against human endoglin (CD105)", Biochimica et Biophysica Acta 1663, pp. 158-166 (2004).
International Search Report for PCT/US2009/054765, mailed Aug. 25, 2010, 16 pgs.
Batinić-Haberle et al., "Superoxide Dismutase Mimics: Chemistry, Pharmacology, and Therapeutic Potential", 2010, *Antioxid Redox Signal.* 13:877-918.
Yamamoto et al., "Nitric Oxide Donors", 2000, *Proc. Soc. Exptl. Biol. & Med.*, 225:200-206.

* cited by examiner

*Primary Examiner* — Richard Schnizer
*Assistant Examiner* — Alma Pipic
(74) *Attorney, Agent, or Firm* — Squire Sanders (US) LLP

(57) ABSTRACT

A coating on a balloon of a medical device is provided. The coating comprises a drug and a polymer. Also provided are methods of forming and using the coating.

24 Claims, No Drawings

COATING ON A BALLOON COMPRISING A POLYMER AND A DRUG

BACKGROUND OF THE INVENTION

1. Field of the Invention

This invention generally relates to a coating containing a drug on a balloon device.

2. Description of the Background

Percutaneous coronary intervention (PCI) is a procedure for treating heart disease. A catheter assembly having a balloon portion is introduced percutaneously into the cardiovascular system of a patient via the radial, brachial or femoral artery. The catheter assembly is advanced through the coronary vasculature until the balloon portion is positioned across the occlusive lesion. Once in position across the lesion, the balloon is inflated to a predetermined size to radially compress the atherosclerotic plaque of the lesion to remodel the lumen wall. The balloon is then deflated to a smaller profile to allow the catheter to be withdrawn from the patient's vasculature.

Problems associated with the above procedure include formation of intimal flaps or torn arterial linings which can collapse and occlude the blood conduit after the balloon is deflated. Moreover, thrombosis and restenosis of the artery may develop over several months after the procedure, which may require another angioplasty procedure or a surgical bypass operation. To reduce the partial or total occlusion of the artery by the collapse of the arterial lining and to reduce the chance of thrombosis or restenosis, a stent is implanted in the artery to keep the artery open. Drug delivery stents have reduced the incidence of in-stent restenosis (ISR) after PCI (see, e.g., Serruys, P. W., et al., J. Am. Coll. Cardiol. 39:393-399 (2002)), which has plagued interventional cardiology for more than a decade. However, a few challenges remain in the art of drug delivery stents. A significant concern with respect to stenting is late stent thrombosis for drug eluting stents. The incidence appears to be higher for drug delivery stents than the corresponding bare metal stents (BMSs). Potential causes for this phenomenon are: (1) reduced or delayed healing due to the presence of the anti-proliferative drug, and (2) a chronic inflammatory or hypersensitivity response to the polymeric coating on a drug delivery stent.

An alternative currently being pursued is a drug coated balloon (DCB) onto which is crimped a bare metal stent. Such a system provides a burst release of the majority of the drug and has no permanent polymer, and hence any concern over the polymer is removed. Issues with this approach include drug loss from abrasion and delivery of the crimped/folded stent/balloon to the lesion and drug loss by hydration and diffusion from the drug coated balloon during transit from the RHV (rotating hemostasic valve) to the lesion.

A drug coated balloon may also be used separately to treat a lesion. After treatment a stent may optionally be placed. In this case, no stent is present on the balloon with the advantage of increased drug coated balloon area to transfer drug to tissue. While this alleviates any concerns with drug or coating loss from stent crimping and assembly operations, it leaves the balloon coating more unprotected during the system delivery through the RHV, through tortuous anatomy, or through previously deployed stents.

There are many schemes to place a drug onto a balloon. The simplest is to coat the pure drug. Another simple approach is Scheller's scheme, which is to coat the drug with a binder of Ultravist non-ionic contrast agent. These sorts of coatings certainly release the drug rapidly upon exposure to the aqueous environment. However, we would not expect them to be particularly abrasion resistant, or to have good mechanical properties. Abrasion resistance comes into play when the stent is crimped on and when subjected to the rigors of device delivery. If the mechanical properties are poor with regards to adhesion and ultimate elongation, then the coating will crack and displace when the balloon is expanded. It does minimal good if, when expanded; the coating immediately sloughs off and washes distally.

Another approach is to use a balloon coating similar to what is utilized current for drug eluting stents. These coatings are biocompatible, and if they could maintain mechanical integrity on an expanded balloon, they would be viable candidates. The main problem is that they don't release the drug quickly enough. These coatings are designed to release the drug over a timeframe of weeks to months. Consequently, they are hydrophobic, have low water absorption, and have only moderate diffusivity to the drug. They release only a small fraction of the drug during a 30-60 second balloon inflation.

As the water the absorption of a coating greatly accelerates drug release, the drug may be combined with a water soluble binder. This can serve to enhance the mechanical properties compared to a coating of pure drug, and assist with dissolution of the drug into solution and removal from the hydrophobic balloon. Water soluble polymers absorb water quickly and as the DCB is resident for such a short time, rapid release of drug in minutes is desirable. Most water soluble polymers are water soluble by virtue of hydrogen bonding, or the presence of polar groups. This behavior often results in a high $T_g$ for these polymers when dry. This property in turn makes the polymers brittle when dry. A summary of the $T_g$s for some common water soluble polymers are shown in Table 1.

| Polymer | T (° C.) |
| --- | --- |
| Poly(vinyl pyrrolidone) | 165 |
| Poly(2-hydroxyethylmethacrylate) | 85 |
| Poly(vinylpyrrolidone-co-vinyl acetate) | 106 |
| Poly(methacrylic acid) | 228 |
| Pluronics (PEO-PPO-PEO) | varies |
| Poly(vinyl alcohol) | 85 |
| Poly(ethylene glycol) | −41 |

Brittleness is a problem as during the steps of balloon folding, pressing and stent crimping the coating can crack and fall off. PEG coatings are waxy, have mediocre mechanical properties, and actually have stability issues when exposed to ETO or e-beam sterilization as the polymer oxidizes. One solution for brittleness is to plasticize the water soluble coating in order to lower the $T_g$. Examples of such plasticizers are glycerol, propylene glycol, and poly(ethylene glycol). This is a viable solution. The mechanical properties of the coating can be quite good. However, there are issues associated with added plasticizers which can lead to undesirable results. For example, coating plasticizer may migrate into the balloon, or other components of the delivery system. Also, if ETO sterilization is utilized, the plasticizer can be partially removed during vacuum ETO degassing, and reaction of the plasticizer with ETO can also be problematic as plasticizers with reactive groups can be ethoxylated and such plasticizers can interact with the drug during sterilization. One would next be concerned over any embolic hazards generated by the rapidly dissolving coating.

A possible approach is to use a permanent polymer coating. Such a coating would not generate any embolic hazard and would protect the drug from abrasion during crimping and system delivery. However, the hydrophobic durable coating simply don't release fast enough, and the water soluble coatings have other issues. Another possibility is to use a coating which is composed of water soluble polymer, but it is crosslinked so that it cannot dissolve. This is a viable option if certain problems were addressed. One problem is carrying out the crosslinking reaction in the presence of the drug. Olimus drugs are fairly sensitive. Crosslinking by thermoset processes which react hydroxyl groups, or UV crosslinking via unsaturation, can both potentially react with olimus drugs, as olimus drugs possess both hydroxyl groups and unsaturation. It is possible that very selective and mild cross-linking chemistries exist which could be done in the presence of an olimus drug, but that is a separate challenge. For example, physical or thermal crosslinking via hydrophilic silk elastin like polymers may allow for a burst release of drug.

Another proposed solution is to use solvent soluble thermoplastic polymers to form a coating on a DCB, but the requirements of rapid drug release combined with good mechanical integrity, both wet and dry, excludes many of these polymers. In addition, the requirement for good mechanical integrity becomes even more challenging when utilizing high drug to polymer ratios to encourage the drug to release quickly. For example, the acrylate family of polymers is broad and versatile. However, the more common hydrophobic members of the acrylate family would not work as a balloon coating. Poly(methyl methacrylate) and poly(ethyl methacrylate) are too brittle and would release the drug too slowly. Poly(n-butyl methacrylate) (PBMA) has a $T_g$ in the range of 20-25° C. (depending on molecular weight), and consequently, is flexible enough to accommodate balloon folding but would still release the drug too slowly as it is hydrophobic with a water absorption of only about 0.4% (see, e.g., Aslamazova et al., Polymer Science USSR, 25(6):1484-1490 (1983)). To increase the drug permeability, an approach would be to lower the $T_g$ further by, e.g., the use of poly(n-hexyl methacrylate) or poly(lauryl methacrylate). The limitations with this approach are (1) that while the drug permeability increases, the materials become very soft and tacky, rendering them not suitable for coating a balloon and (2) that hexyl or lauryl groups are also hydrophobic and of larger steric hindrance than n-butyl, which may counter the beneficial effect of a lower $T_g$ on increasing the drug permeability. As another example, an approach may be to increase the permeability not by lowering the $T_g$, but by increasing the water content by the incorporation of a hydrophilic monomer. However, as described above, the typical hydrophilic monomers with hydrogen bonding and highly polar groups greatly increase the $T_g$ to the point where the polymer is brittle when dry.

Therefore, there is a need for a coating for DCB onto which is crimped a bare metal stent that maintains integrity and provides a burst release of the drug upon deployment of the DCB.

The embodiments below address the above identified issues and needs.

SUMMARY OF THE INVENTION

The present invention provides a medical device and methods of making and using the medical device. The medical device comprises a balloon that comprises a coating on at least a portion of the surface of the balloon. The coating comprises a bioactive agent and a biodurable polymer having a glass transition temperature ($T_g$) below 37° C. when hydrated. the polymer comprises units from an alkoxy acrylate, a methacrylate, vinyl pyrrolidone, or polyethylene glycol acrylate (PEG-acrylate). The coating provides a burst release of the bioactive agent such that upon exposure to a physiological condition a majority of the bioactive agent is released from the coating within a period of about 60 seconds.

In some embodiments, the biodurable polymer can be a homopolymer or copolymer and comprises units from a monomer that can be

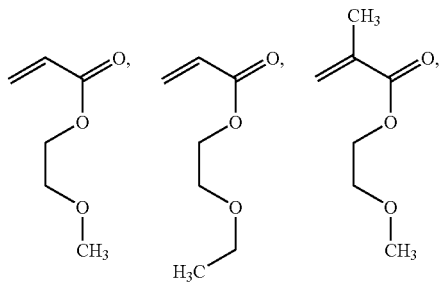

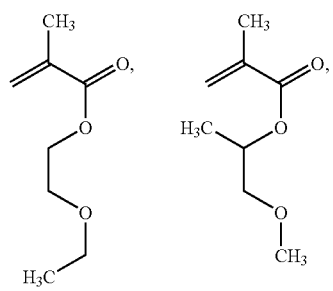

or a combination thereof. In some embodiments, the biodurable polymer has a general structure of

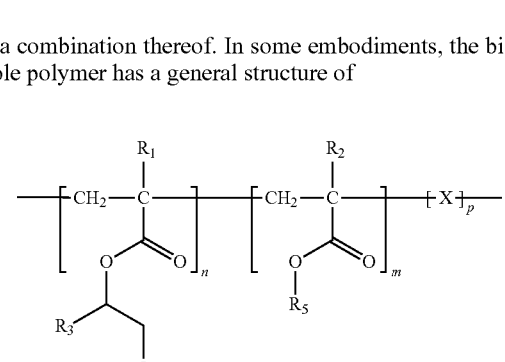

wherein:
$R_1$, $R_2$, and $R_3$ are independently hydrogen or methyl;
$R_4$ is hydrogen, methyl or ethyl;
$R_5$ is any linear, branched, cycloaliphatic, alkene, alkyne, aromatic, or alkyl aromatic moiety with one to sixteen carbons;
n, m, and p are independent integers from 0 to about 100,000;
n+m>0; and
X is absence, vinyl pyrrolidone, or PEG-acrylate.

In some embodiments, in the above polymer, p is a positive integer from 1 to about 100,000, and X is vinyl pyrrolidone or PEG-acrylate. The polymer has the following structure:

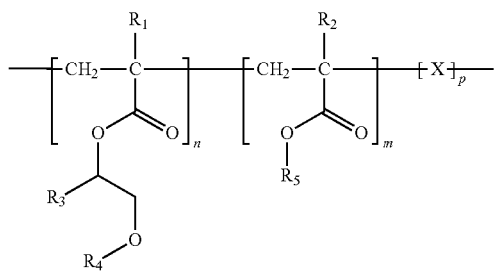

where $R^1$, $R^2$, $R^3$, $R^4$, $R^5$, n, and m are as defined above.

In some embodiments, the bioactive agent can be paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, dexamethasone acetate, corticosteroids, rapamycin, rapamycin derivatives, 40-O-(2-hydroxy)ethyl-rapamycin (everolimus), 40-O-(3-hydroxy)propyl-rapamycin, 40-O-[2-(2-hydroxy) ethoxy]ethyl-rapamycin, and 40-O-tetrazole-rapamycin, 40-epi-(N1-tetrazolyl)-rapamycin (ABT-578), zotarolimus, Biolimus A9 (Biosensors International, Singapore), AP23572 (Ariad Pharmaceuticals), temsirolimus, novolimus, γ-hiridun, clobetasol, pimecrolimus, imatinib mesylate, midostaurin, cRGD, feno fibrate, prodrugs thereof, co-drugs thereof, or combinations thereof. In some embodiments, the bioactive agent is zotarolimus.

In some embodiments, in connection with any or all the above embodiments above, the medical device can include a bare metal stent (BMS) crimped onto the balloon. Measured at 8 months after deployment, the BMS has a late loss in luminal diameter of about 0.5 mm or less, about 0.4 mm or less, about 0.3 mm or less, about 0.2 mm or less, or about 0.1 mm or less.

In some embodiments, the present invention provides a method for fabricating a medical device comprising a balloon. The method comprises forming a coating on at least a portion of the surface of the balloon. The coating is as the coating of the various embodiments of the medical device described above.

In some embodiments, it is provided a method. The method comprises administering to a human being an medical device according to the various embodiments described above for treating, preventing or ameliorating a medical condition such as restenosis, atherosclerosis, acute myocardial infarction, thrombosis, hemorrhage, vascular dissection or perforation, vascular aneurysm, vulnerable plaque, chronic total occlusion, claudication, anastomotic proliferation (for vein and artificial grafts), bile duct obstruction, urethral obstruction, tumor obstruction, or combinations of these.

DETAILED DESCRIPTION OF THE INVENTION

The present invention provides a medical device and methods of making and using the medical device. The medical device comprises a balloon that comprises a coating on at least a portion of the surface of the balloon. The coating comprises a bioactive agent and a biodurable polymer having a glass transition temperature ($T_g$) below 37° C. when hydrated. the polymer comprises units from an alkoxy acrylate, a methacrylate, vinyl pyrrolidone, or PEG-acrylate. The coating provides a burst release of the bioactive agent such that upon exposure to a physiological condition a majority of the bioactive agent is released from the coating within a period of about 60 seconds. The biodurable polymer can be a homopolymer or copolymer. The bioactive agent can be any agent that imparts therapeutic effect to a patient receiving the agent. In some embodiments, the bioactive agent is zotarolimus.

In some embodiments, in connection with any or all the above embodiments above, the medical device can include a bare metal stent (BMS) crimped onto the balloon. Measured at 8 months after deployment, the BMS has a late loss in luminal diameter of about 0.5 mm or less, about 0.4 mm or less, about 0.3 mm or less, about 0.2 mm or less, or about 0.1 mm or less.

In some embodiments, the present invention provides a method for fabricating a medical device comprising a balloon. The method comprises forming a coating on at least a portion of the surface of the balloon. The coating is as the coating of the various embodiments of the medical device described herein.

In some embodiments, it is provided a method. The method comprises administering to a human being an medical device according to the various embodiments described herein for treating, preventing or ameliorating a medical condition such as restenosis, atherosclerosis, acute myocardial infarction, thrombosis, hemorrhage, vascular dissection or perforation, vascular aneurysm, vulnerable plaque, chronic total occlusion, claudication, anastomotic proliferation (for vein and artificial grafts), bile duct obstruction, urethral obstruction, tumor obstruction, or combinations of these.

The medical devices described herein are advantageous over the existing technology. The DCB comprises a coating which provides a burst release of the drug off the DCB and that substantially maintains coating integrity upon DCB deployment. The coating has good mechanical integrity dry and hydrated including low particulate hazard and releases the drug quickly in seconds or minutes upon inflation. Advantageous features of such a coating include, among others:
(a) the coating can be thermoplastic or plastic with no crosslinking required;
(b) the coating can be formed using conventional coating techniques such as coating with a solvent (solvent applied);
(c) the coating is sterilizable, e.g., sterilizable by ETO;
(d) adheres well to balloon; and
(e) is hemocompatible and biocompatible.

Definitions

Wherever applicable, the definitions to some terms used throughout the description of the present invention as provided below shall apply.

The terms "biologically degradable" (or "biodegradable"), "biologically erodable" (or "bioerodable"), "biologically absorbable" (or "bioabsorbable"), and "biologically resorbable" (or "bioresorbable"), in reference to polymers and coatings, are used interchangeably and refer to polymers and coatings that are capable of being completely or substantially completely degraded, dissolved, and/or eroded over time when exposed to physiological conditions and can be gradually resorbed, absorbed and/or eliminated by the body, or that can be degraded into fragments that can pass through the kidney membrane of an animal (e.g., a human), e.g., fragments having a molecular weight of about 40,000 Daltons (40 K Daltons) or less. The process of breaking down and eventual absorption and elimination of the polymer or coating can be caused by, e.g., hydrolysis, metabolic processes, oxidation, enzymatic processes, bulk or surface erosion, and the like. Conversely, a "biostable" polymer or coating refers to a durable polymer or coating that is not biodegradable.

Whenever the reference is made to "biologically degradable," "biologically erodable," "biologically absorbable," and "biologically resorbable" stent coatings or polymers forming such stent coatings, it is understood that after the process of degradation, erosion, absorption, and/or resorption has been completed or substantially completed, no coating or substantially little coating will remain on the stent. "Physiological conditions" refer to conditions to which an implant is exposed within the body of an animal (e.g., a human). Physiological conditions include, but are not limited to, "normal" body temperature for that species of animal (approximately 37° C. for a human) and an aqueous environment of physiologic ionic strength, pH and enzymes. In some cases, the body temperature of a particular animal may be above or below what would be considered "normal" body temperature for that species of animal. For example, the body temperature of a human may be above or below approximately 37° C. in certain cases. The scope of the present invention encompasses such cases where the physiological conditions (e.g., body temperature) of an animal are not considered "normal."

In the context of a blood-contacting medical device, a "prohealing" drug or agent refers to a drug or agent that has the property that it promotes or enhances re-endothelialization of arterial lumen to promote healing of the vascular tissue.

As used herein, a "co-drug" is a drug that is administered concurrently or sequentially with another drug to achieve a particular pharmacological effect. The effect may be general or specific. The co-drug may exert an effect different from that of the other drug, or it may promote, enhance or potentiate the effect of the other drug.

As used herein, the term "prodrug" refers to an agent rendered less active by a chemical or biological moiety, which metabolizes into or undergoes in vivo hydrolysis to form a drug or an active ingredient thereof. The term "prodrug" can be used interchangeably with terms such as "proagent", "latentiated drugs", "bioreversible derivatives", and "congeners". N. J. Harper, Drug latentiation, *Prog Drug Res.,* 4: 221-294 (1962); E. B. Roche, Design of Biopharmaceutical Properties through Prodrugs and Analogs, Washington, D.C.: American Pharmaceutical Association (1977); A. A. Sinkula and S. H. Yalkowsky, Rationale for design of biologically reversible drug derivatives: prodrugs, *J. Pharm. Sci.,* 64: 181-210 (1975). Use of the term "prodrug" usually implies a covalent link between a drug and a chemical moiety, though some authors also use it to characterize some forms of salts of the active drug molecule. Although there is no strict universal definition of a prodrug itself, and the definition may vary from author to author, prodrugs can generally be defined as pharmacologically less active chemical derivatives that can be converted in vivo, enzymatically or nonenzymatically, to the active, or more active, drug molecules that exert a therapeutic, prophylactic or diagnostic effect. Sinkula and Yalkowsky, above; V. J. Stella et al., Prodrugs: Do they have advantages in clinical practice?, *Drugs,* 29: 455-473 (1985).

Unless otherwise specifically defined, the terms "polymer" and "polymeric" refer to compounds that are the product of a polymerization reaction. These terms are inclusive of homopolymers (i.e., addition or condensation polymers obtained by polymerizing one type of monomer), copolymers (i.e., addition or condensation polymers obtained by polymerizing two or more different types of monomers), condensation polymers (polymers made from condensation polymerization, tri-block copolymers, etc., including random (by either addition or condensation polymerization), alternating (by either addition or condensation polymerization), block (by either addition or condensation polymerization), graft, dendritic, crosslinked, blends and any other variations thereof.

As used herein, the term "implantable" refers to the attribute of being implantable in a mammal (e.g., a human being or patient) that meets the mechanical, physical, chemical, biological, and pharmacological requirements of a device provided by laws and regulations of a governmental agency (e.g., the U.S. FDA) such that the device is safe and effective for use as indicated by the device. As used herein, a "medical device" may be any suitable substrate that can be implanted in a human or non-human animal. Examples of medical devices include, but are not limited to, balloon catheters, self-expandable stents, balloon-expandable stents, coronary stents, peripheral stents, stent-grafts, catheters, other expandable tubular devices for various bodily lumen or orifices, grafts, vascular grafts, arterio-venous grafts, by-pass grafts, pacemakers and defibrillators, leads and electrodes for the preceding, artificial heart valves, anastomotic clips, arterial closure devices, patent foramen ovale closure devices, cerebrospinal fluid shunts, and particles (e.g., drug-eluting particles, microparticles and nanoparticles). The stents may be intended for any vessel in the body, including neurological, carotid, vein graft, coronary, aortic, renal, iliac, femoral, popliteal vasculature, and urethral passages. An medical device can be designed for the localized delivery of a therapeutic agent. A medicated medical device may be constructed in part, e.g., by coating the device with a coating material containing a therapeutic agent. The body of the device may also contain a therapeutic agent. In the context of being implantable and the medical device described herein, the term "implanting" is used interchangeably with the term "administering" or "deploying", and the term "implantation" is used interchangeably with the term "administration" or "deployment."

As used herein, the term "majority" shall mean a population or amount of over 50% of total bioactive agent in the coating on the DCB. In some embodiments, the term "majority" shall mean a population or amount of about 51%, about 60%, about 65%, about 70%, about 75%, about 80%, about 85%, about 90%, about 95%, or about 99% of total amount of the bioactive agent in the coating on the DCB.

As used herein, a material that is described as a layer or a film (e.g., a coating) "disposed over" an indicated substrate (e.g., a medical device) refers to, e.g., a coating of the material deposited directly or indirectly over at least a portion of the surface of the substrate. Direct depositing means that the coating is applied directly to the exposed surface of the substrate. Indirect depositing means that the coating is applied to an intervening layer that has been deposited directly or indirectly over the substrate. In some embodiments, the term a "layer" or a "film" excludes a film or a layer formed on a non-medical device.

In the context of a stent, "delivery" refers to introducing and transporting the stent through a bodily lumen to a region, such as a lesion, in a vessel that requires treatment. "Deployment" corresponds to the inflation of the balloon and expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

Biodurable Polymers

In some embodiments, the coating comprises a polymer formed from monomers which are hydrophilic, but which do not result in polymers that have high $T_g$s. One such group are the polymers synthesized from alkoxy acrylates. These include methoxy ethyl acrylate (MEA), ethoxyethyl acrylate (EEA), methoxyethyl methacrylate (MOEMA) and ethoxyethyl methacrylate (EDEMA). The alkoxy structure confers a degree of hydrophilicity that can be used to increase the water swelling of the polymer, which increases the drug permeability. The glass transition temperatures for the polymers of the above monomers are −50° C. for MEA and EEA, 16° C. for MEM, the $T_g$ for EOEMA should be slightly lower than 16° C., and the $T_g$ of the last polymer has not been measured. These Tgs indicate that these polymers will all be flexible when dry at room temperature.

In some embodiments, the coating can comprise a polymer formed from alkoxy acrylate. The alkoxy acrylates, particularly poly(2-methoxyethyl acrylate) and poly(2-methoxyethyl methacrylate) are hydrophilic but without having a high $T_g$ when dry which would make them brittle. Yet, their hydrophilicity will allow enough water absorption for them to rapidly release an olimus drug. They are thermoplastic and can be solution processed. In addition, the low $T_g$ and structure impart adhesion with the balloon to the polymers.

Considering the chemical structures of the alkoxy acrylates, one can see that these compounds contain the smallest PEG-type group possible. A single alkyloxyethyl group PEG is known for its non-fouling or protein repelling properties. 2-methoxyethyl acrylate (MEA), has been extensively studied for blood contacting applications. Tanaka et al. for example, compared the thrombogenicity of poly(2-methoxyethyl acrylate) (PMEA), poly(2-hydroxyethyl methacrylate) (PHEMA), poly(2-hydroxyethyl acrylate) (PHEA), and other alkyl methacrylates (Tanaka et al., Biomaterials, 21:1471-1481 (2000)). Several measures of in vitro hemocompatibility, including human platelet adhesion, changes in platelet morphology, total absorbed protein from human plasma, amount of absorbed BSA, absorbed human fibrinogen, and changes in protein conformation by circular dichroism were measured, showing the PMEA coating being the most hemocompatible of the polymers tested (Id.). Kocakulak et al., investigated the blood compatibility of PMEA coated extracorporeal circuits (Kocakulak, et al., J. Bioactive and Compatible Polymers, 17:33 (2002)). Hollow fiber oxygenators coated with PMEA were evaluated during twenty clinical procedures requiring cardiopulmonary bypass. The operations were compared to twenty operations with uncoated hollow fiber oxygenators. PMEA coatings were found to reduce both platelet adhesion and fibrinogen/albumin adsorption. A coating of PEMA, known as the X Coating™, is used in the CAPIOX RX blood oxygenator sold by Terumo. The acute biocompatibility of EOEMA is good as indicated by its use in contact lenses.

Some exemplary alkoxy acrylates are listed again below:

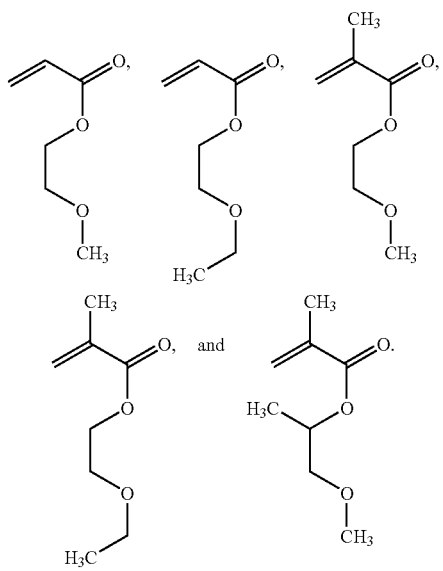

Of these, all are commercially available except for the last one. They are readily polymerized into polymers using either free radical, ionic polymerization and atom transfer radical polymerization (ATRP). The above alkoxy acrylates can also be copolymerized with alkyl acrylates, vinyl pyrrolidone or PEG-acrylates. Polymerization with alkyl acrylates would primarily be done to moderate the water absorption or increase adhesion to the balloon. Addition of PEG-acrylates or vinyl pyrrolidone will increase the water adsorption further.

In some embodiments, the biodurable polymer can be a homopolymer or copolymer and comprises units from a monomer that can be

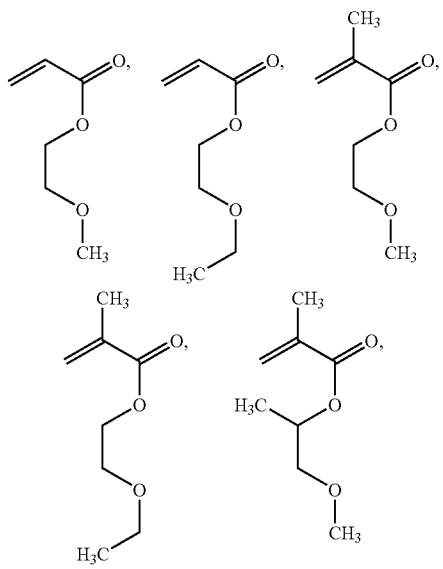

or a combination thereof. In some embodiments, the biodurable polymer has a general structure of

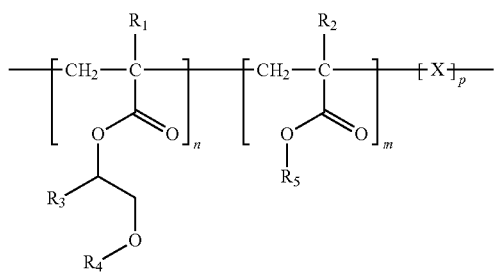

wherein:
$R_1$, $R_2$, and $R_3$ are independently hydrogen or methyl;
$R_4$ is hydrogen, methyl or ethyl;
$R_5$ is any linear, branched, cycloaliphatic, alkene, alkyne, aromatic, or alkyl aromatic moiety with one to sixteen carbons;
n, m, and p are independent integers from 0 to about 100,000; n+m>0; and
X is absence, vinyl pyrrolidone, or PEG-acrylate.

In some embodiments, in the above polymer, p is a positive integer from 1 to about 100,000, and X is vinyl pyrrolidone or PEG-acrylate. The polymer has the following structure:

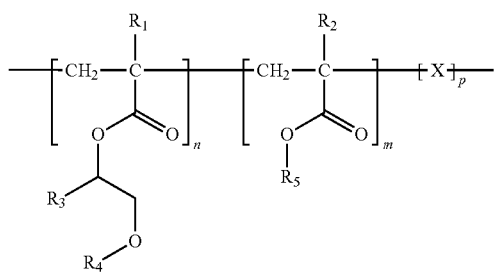

where $R^1$, $R^2$, $R^3$, $R^4$, $R^5$, n, and m are as defined above.

The useful monomer ratio range of the alkoxy acrylate, which is more hydrophilic, to the more hydrophobic, non-alkoxy acrylate is 50/50 to 1/99 (mole/mole). Specific hydrophobic methacrylates would include ethyl methacrylate, n-propyl methacrylate, isopropyl methacrylate, isobutyl methacrylate, sec-butyl methacrylate, 2-ethyl-hexyl methacrylate, n-hexyl methacrylate, cyclohexyl methacrylate, n-hexyl methacrylate, isobornyl methacrylate, methyl methacrylate and trimethylcyclohexyl methacrylate. In all of these copolymer compositions, we target a monomer ratio so that the copolymer $T_g$, when hydrated, is less than 37° C. This hydrated, copolymer $T_g$ can be calculated using the Fox equation:

$$\frac{1}{T_g^{Polymer}} = \frac{W^{PM}}{T_g^{PM}} + \frac{W^{Water}}{T_g^{Water}} + \frac{W^{Methacrylate}}{T_g^{Methacrylate}}$$

$$\frac{1}{T_g^{Polymer}} = \frac{W^{AA}}{T_g^{AA}} + \frac{W^{Water}}{T_g^{Water}} + \frac{W^{Methacrylate}}{T_g^{Methacrylate}}$$

Where $T_g$=Glass transition temperature of the homopolymer or pure material. In the case of water, −40° C.; and W=Weight fraction of the components, and $T_g^{AA}$ is the $T_g$ of the alkoxy acrylate.

Hence, once the water absorption of the polymer is known, which is usually measured experimentally, the copolymer $T_g$ can be estimated with the desired target of <37° C. With a design $T_g$ of less than 37° C., the copolymer will have a high degree of polymer mobility when placed in vivo.

Methods of Fabricating

In according to a further aspect of the present invention, it is provided a method of fabricating a medical device comprising a balloon. The method comprises forming a coating on the balloon, the coating comprising a polymer described herein.

In this invention drug can be loaded into the polymer in a matrix form at various drug to polymer ratios. Another option would be to spray drug directly on the balloon and then topcoat with a thin layer of hydrophilic alkoxy acrylate polymer. Thirdly, drug can be combined with various different polymers in solution form where these polymers span a range of water absorption. These solutions can then be sequentially sprayed either in order of lowest to highest water absorption to produce the desired effect. In another embodiment different alkoxy acrylate polymers may be blended to produce the desired water absorption effect. These materials can also be blended with various other materials such as hydrophobic methacrylates, other hydrophilic polymers or plasticizers for the desired effect.

Sterilization of a coated medical device generally involves a process for inactivation of micropathogens. Such processes are well known in the art. A few examples are e-beam, ETO sterilization, and gamma irradiation. Most, if not all, of these processes can involve an elevated temperature. For example, ETO sterilization of a coated stent generally involves heating above 50° C. at humidity levels reaching up to 100% for periods of a few hours up to 24 hours. A typical EtO cycle would have the temperature in an enclosed chamber reach as high as above 50° C. within the first 3-4 hours then and fluctuate between 40° C. to 50° C. for 17-18 hours while the humidity would reach a peak at 100% and then maintain above 80% during the fluctuation time of the cycle.

Some examples of the drug or bioactive agent that can be included in the coating on a DCB can be paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, dexamethasone acetate, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), zotarolimus, Biolimus A9 (Biosensors International, Singapore), AP23572 (Ariad Pharmaceuticals), temsirolimus, novolimus, γ-hiridun, clobetasol, pimecrolimus, imatinib mesylate, midostaurin, feno fibrate, prodrugs thereof, co-drugs thereof, and combinations thereof.

Drug or Biologically Active Agents

The medical device described herein can include at least one drug or biologically active ("bioactive") agent. The at least one drug bioactive agent can include any substance capable of exerting a therapeutic, prophylactic or diagnostic effect for a patient. As used herein, the term drug and bioactive agent are used interchangeably.

Examples of suitable bioactive agents include, but are not limited to, synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules that bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. The bioactive agents could be designed, e.g., to inhibit the activity of vascular smooth muscle cells. They could be directed at inhibiting abnormal or inappropriate migration and/or proliferation of smooth muscle cells to inhibit restenosis.

In certain embodiments, optionally in combination with one or more other embodiments described herein, the medical device can include at least one biologically active agent selected from antiproliferative, antineoplastic, antimitotic, anti-inflammatory, antiplatelet, anticoagulant, antifibrin, antithrombin, antibiotic, antiallergic and antioxidant substances.

An antiproliferative agent can be a natural proteineous agent such as a cytotoxin or a synthetic molecule. Examples of antiproliferative substances include, but are not limited to, actinomycin D or derivatives and analogs thereof (manufactured by Sigma-Aldrich, or COSMEGEN available from Merck) (synonyms of actinomycin D include dactinomycin, actinomycin IV, actinomycin $I_1$, actinomycin $X_1$, and actinomycin $C_1$); all taxoids such as taxols, docetaxel, and paclitaxel and derivatives thereof; all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Examples of rapamycin derivatives include, but are not limited to, 40-O-(2-hydroxy)ethyl-rapamycin (trade name everolimus from Novartis), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus, manufactured by Abbott Labs.), Biolimus A9 (Biosensors International, Singapore), AP23572 (Ariad Pharmaceuticals), temsirolimus, novolimus, prodrugs thereof, co-drugs thereof, and combinations thereof.

An anti-inflammatory drug can be a steroidal anti-inflammatory drug, a nonsteroidal anti-inflammatory drug (NSAID), or a combination thereof. Examples of anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol, clobetasol propionate, clobetasone butyrate, clopirac, cloticasone propionate, cormethasone acetate, cortodoxone, deflazacort, desonide, desoximetasone, dexamethasone, dexamethasone acetate, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

Alternatively, the anti-inflammatory agent can be a biological inhibitor of pro-inflammatory signaling molecules. Anti-inflammatory biological agents include antibodies to such biological inflammatory signaling molecules.

In addition, the bioactive agents can be other than antiproliferative or anti-inflammatory agents. The bioactive agents can be any agent that is a therapeutic, prophylactic or diagnostic agent. In some embodiments, such agents can be used in combination with antiproliferative or anti-inflammatory agents. These bioactive agents can also have antiproliferative and/or anti-inflammatory properties or can have other properties such as antineoplastic, antimitotic, cystostatic, antiplatelet, anticoagulant, antifibrin, antithrombin, antibiotic, antiallergic, and/or antioxidant properties.

Examples of antineoplastics and/or antimitotics include, but are not limited to, paclitaxel (e.g., TAXOL® available from Bristol-Myers Squibb), docetaxel (e.g., Taxotere® from Aventis), methotrexate, azathioprine, vincristine, vinblastine, fluorouracil, doxorubicin hydrochloride (e.g., Adriamycin® from Pfizer), and mitomycin (e.g., Mutamycin® from Bristol-Myers Squibb).

Examples of antiplatelet, anticoagulant, antifibrin, and antithrombin agents that can also have cytostatic or antiproliferative properties include, but are not limited to, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as ANGIOMAX (from Biogen), calcium channel blockers (e.g., nifedipine), colchicine, fibroblast growth factor (FGF) antagonists, fish oil (e.g., omega 3-fatty acid), histamine antagonists, lovastatin (a cholesterol-lowering drug that inhibits HMG-CoA reductase, brand name Mevacor® from Merck), monoclonal antibodies (e.g., those specific for platelet-derived growth factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetics, 4-amino-2,2,6,6-tetramethylpiperidine-1-oxyl (4-amino-TEMPO), estradiol, anticancer agents, dietary supplements such as various vitamins, and a combination thereof.

Examples of cytostatic substances include, but are not limited to, angiopeptin, angiotensin converting enzyme inhibitors such as captopril (e.g., Capoten® and Capozide® from Bristol-Myers Squibb), cilazapril and lisinopril (e.g., Prinivil® and Prinzide® from Merck).

Examples of antiallergic agents include, but are not limited to, permirolast potassium. Examples of antioxidant substances include, but are not limited to, 4-amino-2,2,6,6-tetramethylpiperidine-1-oxyl (4-amino-TEMPO). Other bioactive agents include anti-infectives such as antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary vasodilators; peripheral and cerebral vasodilators; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents.

Other biologically active agents that can be used include alpha-interferon, genetically engineered epithelial cells, tacrolimus and dexamethasone.

A "prohealing" drug or agent, in the context of a blood-contacting medical device, refers to a drug or agent that has the property that it promotes or enhances re-endothelialization of arterial lumen to promote healing of the vascular tissue. The portion(s) of a medical device (e.g., a stent) containing a prohealing drug or agent can attract, bind, and eventually become encapsulated by endothelial cells (e.g., endothelial progenitor cells). The attraction, binding, and encapsulation of the cells will reduce or prevent the formation of emboli or thrombi due to the loss of the mechanical properties that could occur if the stent was insufficiently encapsulated. The enhanced re-endothelialization can promote the endothelialization at a rate faster than the loss of mechanical properties of the stent.

The prohealing drug or agent can be dispersed in the body of the bioabsorbable polymer substrate or scaffolding. The prohealing drug or agent can also be dispersed within a bioabsorbable polymer coating over a surface of an medical device (e.g., a stent).

"Endothelial progenitor cells" refer to primitive cells made in the bone marrow that can enter the bloodstream and go to areas of blood vessel injury to help repair the damage. Endothelial progenitor cells circulate in adult human peripheral blood and are mobilized from bone marrow by cytokines, growth factors, and ischemic conditions. Vascular injury is repaired by both angiogenesis and vasculogenesis mechanisms. Circulating endothelial progenitor cells contribute to repair of injured blood vessels mainly via a vasculogenesis mechanism.

In some embodiments, the prohealing drug or agent can be an endothelial cell (EDC)-binding agent. In certain embodiments, the EDC-binding agent can be a protein, peptide or antibody, which can be, e.g., one of collagen type 1, a 23 peptide fragment known as single chain Fv fragment (scFv A5), a junction membrane protein vascular endothelial (VE)-cadherin, and combinations thereof. Collagen type 1, when bound to osteopontin, has been shown to promote adhesion of endothelial cells and modulate their viability by the down regulation of apoptotic pathways. S. M. Martin, et al., *J. Biomed. Mater. Res.*, 70A:10-19 (2004). Endothelial cells can be selectively targeted (for the targeted delivery of immunoliposomes) using scFv A5. T. Volkel, et al., *Biochimica et Biophysica Acta,* 1663:158-166 (2004). Junction membrane protein vascular endothelial (VE)-cadherin has been shown to bind to endothelial cells and down regulate apoptosis of the endothelial cells. R. Spagnuolo, et al., *Blood,* 103:3005-3012 (2004).

In a particular embodiment, the EDC-binding agent can be the active fragment of osteopontin, (Asp-Val-Asp-Val-Pro-Asp-Gly-Asp-Ser-Leu-Ala-Try-Gly). Other EDC-binding agents include, but are not limited to, EPC (epithelial cell) antibodies, RGD peptide sequences, RGD mimetics, and combinations thereof.

In further embodiments, the prohealing drug or agent can be a substance or agent that attracts and binds endothelial progenitor cells. Representative substances or agents that attract and bind endothelial progenitor cells include antibodies such as CD-34, CD-133 and VEGF type 2 receptor. An agent that attracts and binds endothelial progenitor cells can include a polymer having nitric oxide donor groups.

The foregoing biologically active agents are listed by way of example and are not meant to be limiting. Other biologically active agents that are currently available, or that may be developed in the future, are equally applicable.

In a more specific embodiment, optionally in combination with one or more other embodiments described herein, the medical device of the invention comprises at least one biologically active agent selected from paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, dexamethasone acetate, rapamycin, rapamycin derivatives, 40-O-(2-hydroxy)ethyl-rapamycin (everolimus), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), Biolimus A9 (Biosensors International, Singapore), AP23572 (Ariad Pharmaceuticals), temsirolimus, novolimus, pimecrolimus, imatinib mesylate, midostaurin, clobetasol, progenitor cell-capturing antibodies, prohealing drugs, prodrugs thereof, co-drugs thereof, and a combination thereof. In a particular embodiment, the bioactive agent is zotarolimus. In another specific embodiment, the bioactive agent is clobetasol.

An alternative class of drugs would be p-para-α-agonists for increased lipid transportation, examples include fenofibrate.

In some embodiments, optionally in combination with one or more other embodiments described herein, the at least one biologically active agent specifically cannot be one or more of any of the bioactive drugs or agents described herein.

Method of Treating or Preventing Disorders

The coated balloon described herein could be used in any part of the vasculature or tubular structure in the body including neurological, carotid, coronary, aorta, renal, biliary, ureter, iliac, femoral, and popliteal vessels. It may also be used prior to, after, or in conjunction with a stent that may be self-expanding or balloon expandable. Polymer composition and molecular weight can also be controlled to minimize adhesion to the stent. These alkoxy acrylate polymer balloon coatings may also be used on balloons which are then covered with a porous membrane, capsule, or, sleeve. In some cases the sleeve itself can be fabricated from this polymer class as well.

A medical device according to the present invention can be used to treat, prevent or diagnose various conditions or disorders. Examples of such conditions or disorders include, but are not limited to, atherosclerosis, acute myocardial infarction, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, urethral obstruction and tumor obstruction. A portion of the medical device or the whole device itself can be formed of the material, as described herein. For example, the material can be a coating disposed over at least a portion of the device.

In certain embodiments, optionally in combination with one or more other embodiments described herein, the inventive method treats, prevents or diagnoses a condition or disorder selected from atherosclerosis, acute myocardial infarction, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, urethral obstruction and tumor obstruction. In a particular embodiment, the condition or disorder is atherosclerosis, thrombosis, restenosis or vulnerable plaque.

In some embodiments, the vascular medical condition or vascular condition is a coronary artery disease (CAD) and/or a peripheral vascular disease (PVD).

In one embodiment of the method, optionally in combination with one or more other embodiments described herein, the medical device includes a coating containing at least one biologically active agent selected from paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, dexamethasone acetate, rapamycin, rapamycin derivatives, 40-O-(2-hydroxy)ethyl-rapamycin (everolimus), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), Biolimus A9 (Biosensors International, Singapore), AP23572 (Ariad Pharmaceuticals), temsirolimus, novolimus, pimecrolimus, imatinib mesylate, midostaurin, clobetasol, progenitor cell-capturing antibodies, prohealing drugs, fenofibrate, prodrugs thereof, co-drugs thereof, and a combination thereof.

In certain embodiments, optionally in combination with one or more other embodiments described herein, the medical device used in the method can include a component selected from balloon catheters, stents, grafts, stent-grafts, catheters, leads and electrodes, clips, shunts, closure devices, valves, and particles. In a specific embodiment, the medical device comprises a drug coated balloon and a bare metal stent, where the stent is crimped onto the drug coated balloon.

While particular embodiments of the present invention have been shown and described, it will be obvious to those skilled in the art that changes and modifications can be made without departing from this invention in its broader aspects. Therefore, the claims are to encompass within their scope all such changes and modifications as fall within the true spirit and scope of this invention.

The invention claimed is:

1. A medical device, comprising a balloon that comprises a coating on at least a portion of the surface of the balloon,
wherein the coating comprises a bioactive agent and a biodurable polymer having a glass transition temperature ($T_g$) below 37° C. when hydrated,
wherein the polymer comprises units from an alkoxy acrylate, a methacrylate, vinyl pyrrolidone, or polyethylene glycol acrylate (PEG-acrylate), and
wherein alkoxy acrylate and methacrylate are present at a ratio between 50/50 and 1/99 (mole/mole).

2. The medical device of claim 1, wherein the biodurable polymer comprises units from a monomer selected from the group consisting of

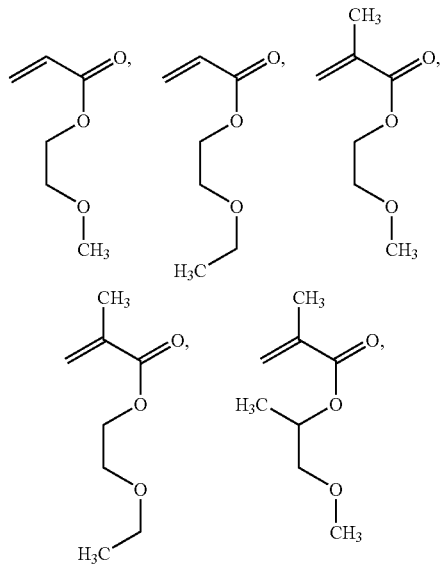

and a combination thereof.

3. The medical device of claim 1, wherein the biodurable polymer has a general structure of

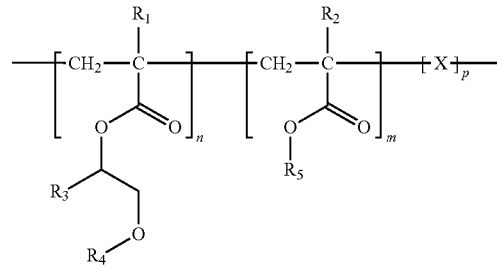

wherein:
$R_1$, $R_2$, and $R_3$ are independently hydrogen or methyl;
$R_4$ is hydrogen, methyl or ethyl;
$R_5$ is any linear, branched, cycloaliphatic, alkene, alkyne, aromatic, or alkyl aromatic moiety with one to sixteen carbons;
n, m, and p are independent integers from 0 to about 100,000;
n+m>0; and
X is absent, vinyl pyrrolidone, or PEG-acrylate.

4. The medical device of claim 1, wherein the bioactive agent is selected from the group consisting of paclitaxel, docetaxel, estradiol, 17-beta-estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, dexamethasone acetate, corticosteroids, rapamycin, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (ABT-578), zotarolimus, umirolimus, temsirolimus, novolimus, γ-hiridun, clobetasol, pimecrolimus, imatinib mesylate, midostaurin, cRGD, fenofibrate, prodrugs thereof, co-drugs thereof, and combinations thereof.

5. The medical device of claim 1, further comprising a bare metal stent (BMS) crimped onto the balloon.

6. The medical device of claim 5, wherein the bioactive agent is zotarolimus.

7. The medical device of claim 6, wherein the BMS has a late loss in luminal diameter of about 0.5 mm or less 8 months after deployment of the BMS.

8. The medical device of claim 6, wherein the BMS has a late loss in luminal diameter of about 0.4 mm or less 8 months after deployment of the BMS.

9. The medical device of claim 6, wherein the BMS has a late loss in luminal diameter of about 0.3 mm or less 8 months after deployment of the BMS.

10. The medical device of claim 6, wherein the BMS has a late loss in luminal diameter of about 0.2 mm or less 8 months after deployment of the BMS.

11. The medical device of claim 6, wherein the BMS has a late loss in luminal diameter of about 0.1 mm or less 8 months after deployment of the BMS.

12. A method for fabricating a medical device comprising a balloon, comprising forming a coating on at least a portion of the surface of the balloon,
    wherein the coating comprises a bioactive agent and a biodurable polymer having a glass transition temperature ($T_g$) below 37° C. when hydrated,
    wherein the polymer comprises units from an alkoxy acrylate, a methacrylate, vinyl pyrrolidone, or polyethylene glycol acrylate (PEG-acrylate), and
    wherein alkoxy acrylate and methacrylate are present at a ratio between 50/50 and 1/99 (mole/mole).

13. The method of claim 12, wherein the biodurable polymer comprises units from a monomer selected from the group consisting of

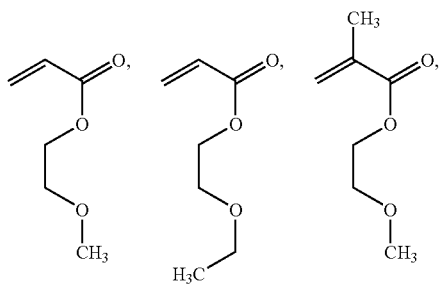

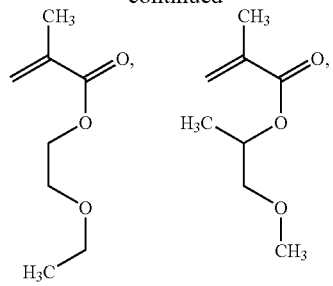

and a combination thereof.

14. The method of claim 12, wherein the biodurable polymer has a general structure of

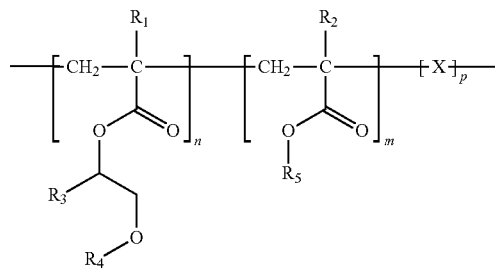

wherein:
    $R_1$, $R_2$, and $R_3$ are independently hydrogen or methyl;
    $R_4$ is hydrogen, methyl or ethyl;
    $R_5$ is any linear, branched, cycloaliphatic, alkene, alkyne, aromatic, or alkyl aromatic moiety with one to sixteen carbons;
    n, m, and p are independent integers from 0 to about 100,000;
    n+m>0; and
    X is absent, vinyl pyrrolidone, or PEG-acrylate.

15. The method of claim 12, wherein the bioactive agent is selected from the group consisting of paclitaxel, docetaxel, estradiol, 17-beta-estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, dexamethasone acetate, corticosteroids, rapamycin, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (ABT-578), zotarolimus, umirolimus, temsirolimus, novolimus, γ-hiridun, clobetasol, pimecrolimus, imatinib mesylate, midostaurin, cRGD, fenofibrate, prodrugs thereof, co-drugs thereof, and combinations thereof.

16. The method of claim 12, further comprising a bare metal stent crimped onto the balloon.

17. The method of claim 16, wherein the bioactive agent is zotarolimus.

18. The medical device of claim 17, wherein the BMS has a late loss in luminal diameter of about 0.5 mm or less 8 months after deployment of the BMS.

19. The medical device of claim 17, wherein the BMS has a late loss in luminal diameter of about 0.4 mm or less 8 months after deployment of the BMS.

20. The medical device of claim 17, wherein the BMS has a late loss in luminal diameter of about 0.3 mm or less 8 months after deployment of the BMS.

21. The medical device of claim 17, wherein the BMS has a late loss in luminal diameter of about 0.2 mm or less 8 months after deployment of the BMS.

22. The medical device of claim 17, wherein the BMS has a late loss in luminal diameter of about 0.1 mm or less 8 months after deployment of the BMS.

23. A method, comprising administering to a human being a medical device according to claim 1 for treating or ameliorating a medical condition selected from the group consisting of restenosis, atherosclerosis, acute myocardial infarction, thrombosis, hemorrhage, vascular dissection or perforation, vascular aneurysm, vulnerable plaque, chronic total occlusion, claudication, anastomotic proliferation, bile duct obstruction, urethral obstruction, tumor obstruction, or combinations of these.

24. A method, comprising administering to a human being a medical device according to claim 6 for treating or ameliorating a medical condition selected from the group consisting of restenosis, atherosclerosis, thrombosis, hemorrhage, vascular dissection or perforation, vascular aneurysm, vulnerable plaque, chronic total occlusion, claudication, anastomotic proliferation, bile duct obstruction, urethral obstruction, tumor obstruction, or combinations of these.

* * * * *